US006864243B1

(12) United States Patent
Peterson (10) Patent No.: US 6,864,243 B1
(45) Date of Patent: Mar. 8, 2005

(54) METHOD FOR TREATING RETINAL DEGENERATION WITH PURINERGIC RECEPTOR AGONISTS

(75) Inventor: Ward M. Peterson, Durham, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/570,231

(22) Filed: May 12, 2000

(51) Int. Cl.[7] .......................... A61K 31/70; C07H 21/00
(52) U.S. Cl. .......................... 514/47; 514/51; 536/25.6
(58) Field of Search ..................... 514/47, 51; 536/25.6

(56) References Cited

U.S. PATENT DOCUMENTS

| 3,846,402 | A | 11/1974 | Eckstein et al. ......... 260/211.5 |
| 5,641,750 | A | 6/1997 | Louis ..................... 514/12 |
| 5,667,968 | A | 9/1997 | LaVail et al. .............. 514/12 |
| 5,763,447 | A | 6/1998 | Jacobus et al. ............ 514/265 |
| 5,837,861 | A | 11/1998 | Pendergast et al. ........ 536/25.6 |
| 5,900,407 | A | 5/1999 | Yerxa et al. ............... 514/47 |
| 6,596,725 | B2 * | 7/2003 | Peterson et al. ........... 514/256 |
| 2001/0031743 | A1 * | 10/2001 | Peterson et al. ............. 514/47 |

FOREIGN PATENT DOCUMENTS

| WO | WO 98/34942 | 8/1998 |
| WO | WO 99/09998 | 4/1999 |
| WO | WO 99/61012 | 12/1999 |
| WO | WO 00/50024 | 8/2000 |
| WO | WO 01/08691 | 2/2001 |

OTHER PUBLICATIONS

Abbracchio, Maria and Geoffrey Burnstock, "Purinergic Signalling: Pathophysiological Roles," *Jpn J Pharmacol*, 78:113–145 (1998).

Abbracchio, M. P. et al., "Effects of ATP Analogues and Basic Fibroblast Growth Factor on Astroglial Cell Differentiation in Primary Cultures of Rat Striatum," *Int J Dev Neurosci*, 13(7):685–693 (1995).

Ambati, Jayakrishna. et al., "Tansscleral Delivery of Bioactive Protein to the Choroid and Retina," *Invest. Ophthalmol. Vis. Sci.*, 41(5):1186–1191 (2000).

Bolego, Chiara. et al., "Characterization of the signalling pathways involved in ATP and basic fibroblast growth factor–induced astrogliosis," *Br J Pharmacol*, 121:1692–1699 (1997).

(List continued on next page.)

*Primary Examiner*—Samuel Barts
*Assistant Examiner*—Howard V. Owens
(74) *Attorney, Agent, or Firm*—Howrey Simon Arnold & White; Viola T. Kung (57) ABSTRACT

The present invention provides a method of preventing or treating retinal degeneration arising from pathophysiological or physical conditions. The method comprises administering to a patient a pharmaceutical composition comprising a purinergic P2Y receptor ligand, in an amount effective to elevate its extracellular concentration to activate retinal glial and neuronal cell surface P2Y receptors and mount a neuroprotective response. Methods of administering including intravitreal bolus and sustained administrations, transscleral delivery, topical, and systemic administrations. The pharmaceutical composition useful in this invention comprises a P2Y purinergic receptor agonist, which include uridine 5'-di-and triphosphate (UDP, UTP) and their analogs, adenosine 5'-diphosphate (ADP) and its analogs, cytidine 5'-di-and triphosphate (CDP, CTP) and their analogs, and dinucleoside polyphosphate compounds.

21 Claims, 2 Drawing Sheets

(2 of 2 Drawing Sheet(s) Filed in Color)

OTHER PUBLICATIONS

Boyer, Jose L. et al., "Identification of potent P2y-purinoceptor agonists that are derivatives of adenosince 5'-monophosphate," Br. J. Pharmacol. 118:1959–1964 (1996).

Bush, Toby G. et al., "Leukocyte Infiltration, Neuronal Degeneration, and Neuite Outgrowth after Ablation of Scar–Forming, Reactive Astrocyted in Adult Transgenic Mice," Neuron, 23:297–302 (1999).

Chen, Yongmei and Albert Y. Sun, "Activation of Transcription Factor AP–1 by Extracellular ATP in PC123 Cells," Neurochem Res,23(4):543–550 (1998).

Eddleston, M. and L. Mucke, "Molecular Profile of Reactive Astrocytes–Implications for their role in Neurologic Disease," Neuroscience, 54(1):15–36 (1993).

Hatten, Mary, et al., "Astroglia in CNS Injury," GLIA, 4:233–243 (1991).

Idestrup, C.P. and M.W. Salter, "P2Y and P2U Receptors Differentially Release Intracellular Ca2+ via the Phospholipase C/Inositol 1,4,5–Triphosphate Pathway in Astrocytes from the Dorsal Spinal Cord," Neuroscience, 86(3):913–923 (1998).

Kandel, Eric and James H. Schwartz, Principles of Neuroscience, 1979, 2nd Ed., Elsevier, New York, (1985).

Kirischuk, S. et al., "Activation of P2–purinoreceptors triggered Ca2+ release from InsP2–sensitive internal stores in mammalian olifodendrocytes," J Physiol (Lond), 483(1):41–57 (1995).

LaVail, Matthew M. et al., "Multiple growth factores, cytokinesm and neurotrophins rescue photoreceptors from the damaging effects of constant light," Proc. Natl Acad Sci., 89:11249–11253 (1992).

Lazarowski, Eduardo. et al., "Pharmacological selectivity of the coloned human P2u–purinoceptor: potent activation by diadenosine tetraphosphate," Brit. J. Pharm. 116:1619–1627 (1995).

Liu, Yao and Masato Wakakura, "P1–/P2–Purinergic Receptors on Cultured Rabbit Retinal Muller Cells," Jpn J Ophthalmol, 42:33–40 (1998).

Lyons, Susan. et al., "Schwann Cells Exhibit P2y Purinergic Receptors that Regulate Intracellular Calcium and Are Up–Regulated by Cyclic AMP Analogues," J Neurochem, 63:552–560 (1994).

Neary, J.T., et al., "Synergistic Activation of DNA Synthesis in Astrocytes by Fibroblast Growth Factors and Extracellular ATP," J Neurochem, 63(2):490–494 (1994).

Neary, Joseph T. and Qing Zhu, "Signaling by ATP receptors in astrocytes," Neuroreport, 5(1315):1617–1620, (1994).

Neary, J. T., et al., "Destabilization of Glial Fibrillary Acidic Protein mRNA in Astrocytes by Ammonia and Protection by Extracellualr ATP," J Neurochem, 63(6):2021–2027 (1994).

Neary, Joseph T., et al., "Mitogenic Signaling by ATP/P2Y Purinergic Receptors in Astocytes: Involvement of a Calcium–Independent Protein Kinase C, Extracellular Signal–Regulated Protein Kinase Pathway Distinct from the Phosphatidylinositol–Specific Phospholipase C/Calcium Pathway," J Neurosci, 19:4211–20, (1999).

Ng, Kam–mui and Leslie E. Orgel, "The action of a water--soluble carbodiimide on adenosine–'5 polyphosphates," Nucleic Acids Res. 15(8):3572–3580 (1987).

Peterson, Ward M., et al., "Extracellualr ATP Activates Calcium Signaling, Ion, and Fluid Transport In Retinal Pigment Epithelium," J Neurosci, 17(7):2324–2337 (1997).

Priller, J., et al., "Stimulation of P2Y–Purinoceptors on Astrocytes Results in Immediate Early Gene Expression and Potentiation of Neuropeptide Action," Neuroscience, 85(2):521–5, 1998.

R.S. Goody and F. Eckstein, "Thiophosphate Analogs of Nucleoside Di– and Triphosphates," J. Am. Chem. Soc. 93: 6252–6257 (1971).

Ralevic, Vera and Geoffrey Burnstock, "Receptors for Purines and Pyrimidines," Pharmacol Rev, 50:413–492 (1998).

Rapaport, Eliezer., et al., "HeLa cell DNA polymerase a is tightly associated with tryptophanyl–tRNA synthetase and diadenosine 5', 5'', –P1, P4–tetraphosphate binding activities," Proc. Natl. Acad. Sci. USA 78(2): 838–842 (1981).

Rathbone, Michael P., et al., "Purine Nucleosides and Nucleotides Stimulate Proliferation of a Wide Range of Cell Types," In Vitro Cell Dev Biol, 28A:529–36, (1992).

Ridet, J.L., et al., "Reactive astrocytes:cellular and molecular cues to biological function," Trands Neurosci, 20(12):570–577 (1997).

Segal, Rosalind A. and Michael E. Greenberg, "Intracellular Signaling Pathways Activated By Neurotrophic Factors," Annu Rev Neurosci,19:463–89, (1996).

Vestn Oftalmol., Jan.–Feb.; :24–6, (1969).

Wu, Delon., et al., Mol Pharmacol,53(2) :346 (1998).

International Search Report.

Sullivan, et al., "Identification and Characterization of $P2Y_2$ Nucleotide Receptors in Human Retinal Pigment Epithelial Cells," Journal of Neuroscience Research 49:43–52 (1997).

* cited by examiner

METHOD FOR TREATING RETINAL DEGENERATION WITH PURINERGIC RECEPTOR AGONISTS

TECHNICAL FIELD

The present invention relates to a method of protecting or delaying retinal neurons from cell death by administering purinergic receptor agonists such as uridine 5'-di-and triphosphates, cytidine 5'-di-and triphosphates, dinucleoside polyphosphates, and their analogs thereof

BACKGROUND OF THE INVENTION

Degeneration of retinal neurons is a debilitating condition and a major cause of irriversible blindness worldwide (National Eye Institute, "Vision Research: A National Plan, 1994–1998"). Retinal degeneration is often an endpoint of a variety of ocular and systemic diseases and environmental conditions. Degenerative retinopathies generally affect two neuronal cell populations in the retina: the photoreceptors and ganglion cells. Degeneration of photoreceptors and ganglion cells can arise from neurodegenerative diseases (macular degeneration, glaucoma, retinitis pigmentosa), optic nerve degeneration and optic neuritis, chronic metabolic diseases (proliferative diabetic retinopathy exposure to neurotoxins, ischemia, and physical trauma (Yanoff and Duker, "Ophthalmology," 8.1.1–8.48.1; National Eye Institute, "Vision Research: A National Plan, 1994–1998").

Previous work has shown that subconjunctival injections of ATP in rabbits result in increased ATP content in the choroid and retina (Dobromyslov et al., Clinical Conference of May 24, 1966). Dobromyslov et al. also show that subconjunctival injection of ATP ameliorated vision loss in patients suffering from maculodystrophy, pigmental dystrophy, complicated myopia and far advanced glaucoma. (*Vestn Oftalmol.*, Jan.–Feb. 24–6, 1969). Dobromyslov et al. state that a direct makeup of energy reserves occurs in subconjunctival administration of ATP because of fast decomposition of ATP in the retina. The authors postulate that the increase in total retinal ATP levels enhances metabolic support of photoreceptors because rhodopsin hydrolyzes ATP and ATP has a well-known role as an energy source in the cell. Currently subconjunctival injection of ATP is not used for treating retinal dystrophies.

To date the methods for treating retinal degenerations are targeted at activating growth factor receptors, such as glial derived neurotrophic factor (GDNF), ciliary neurotrophic factor (CNTF) and brain-derived neurotrophic factor (BDNF) (Louis, U.S. Pat. No. 5,641,750; LaVail., et al., U.S. Pat. No. 5,667,968). The receptor systems employed by these signaling proteins, GDNF, CNTF, and BDNF, are from a receptor class different from the family of P2Y receptors. Currently, these treatments have not been developed for use in the clinic.

Previous work has demonstrated the presence of P2Y receptors in glial and neuronal cells of the mature nervous system (Abbracchio and Burnstock, *Jpn J Pharmacol*, 78:113–45, 1998). P2Y receptors belong to a class of G-protein coupled receptors (GPCR) that activate a variety of intracellular signaling pathways. Although features of P2Y receptor signaling in many cell types are well known, the physiological roles of P2Y receptors in the nervous system are not well-characterized. In central, peripheral and sensory nervous systems, P2Y receptor activation profoundly affect glia, a cell type that plays important roles in nervous system development, function, and survival. Previous work has suggested a role for P2Y receptors in neurotransmission, neuronal-to-glial cell-cell signaling, alterations of gene expression, neuritogenesis, and interactions with growth factors in an additive or synergistic manner (Abbracchio and Burnstock, *Jpn J Pharmacol*, 78:113–45, 1998).

Glial cells in the mature nervous systems provide trophic support to neurons and are therefore a viable cellular target to effect neuronal preservation and survival in a variety of neurodegenerative conditions. Müller cells, astrocytes, and retinal pigment epithelium are three glial cell types in the retina. They form a network of supporting cells around neurons, and this close anatomical proximity is what affords glial cells the capacity to maintain survival and protect neurons. Glial cells provide mechanical support, scavenge debris after neuronal death and injury; provide insulating sheaths for electrical conduction of nerve impulses; buffer extracellular ionic, metabolic, neurotransmitter, and fluid composition; control outgrowth of neurons following injury and death; and provide trophic support for neurons in normal and pathological conditions (Kandel and Schwartz, *Principles of Neuroscience*, 1979, 2nd Ed., Elsevier, New York, 1985). Under conditions of neurological stress and disease, the extracellular environment surrounding neurons and glia are dramatically perturbed, and glial cells contain a wide array of receptors that can integrate this plurality of external stimuli to mount an appropriate, adaptive response (Kandel and Schwartz, Supra). Adenosine 5'-triphosphate (ATP) is a ubiquitous source of cellular energy and is normally contained inside the cells or can be released extracellularly under regulated conditions (Ralevic and Burnstock, *Pharmacol Rev*, 50:413–92, 1998). However, under pathological neurological conditions, ATP is believed to be released in an unregulated capacity from damaged cells and can subsequently activate cell surface ATP receptors on glia (Abbracchio and Burnstock, *Jpn J Pharmacol*, 78:113–45, 1998). The P2Y subtype of nucleotide receptors, which are found on glia, respond to extracellular nucleotides by activating a variety of intracellular signaling pathways and enable the activated glial cell to respond to the underlying neuronal stress and damage (Abbracchio and Burnstock, *Jpn J Pharmacol*, 78:113–45, 1998).

Uridine 5'-triphosphate (UTP) and ATP have been shown to activate the P2Y subtypes of purinergic receptors in multiple glial cells of the central, peripheral, and sensory nervous systems, including oligodendrocytes, astrocytes, Müller cells, retinal pigment epithelium, and resident macrophages (Abbracchio and Burnstock, *Jpn J Pharmacol*, 78:113–45, 1998; Kirischuk, et al., *J Physiol (Lond)*, 483:41–57, 1995; Liu and Wakakura, *Jpn J Ophthalmol*, 42:3340, 1998; Lyons, et al., *J Neurochem*, 63:552–60, 1994; Neary and Zhu, *Neuroreport*, 5:1617–20, 1994; Peterson, et al., *J Neurosci*, 17:2324–37, 1997). Mild mechanical forces have been shown to stimulate ATP release from the retina, which could signal through P2Y receptors on retinal neural and glial cells (Jensen, *IOVS* (suppl.), 40:1237, 1999). Activation of P2Y receptors on glial cells causes concomitant stimulation of phospholipase C and $Ca^{2+}$ release from intracellular stores and activation of intracellular ras-MAPK (mitogen-activated protein kinase) pathway, both of which are linked to cellular differentiation and survival (Idestrup and Salter, *Neuroscience*, 86:913–23, 1998; Neary, et al.,*J Neurosci*, 19:4211–20, 1999; Segal and Greenberg, *Annu Rev Neurosci*, 19:463–89, 1996). Stimulation of DNA synthesis and cell proliferation by purines has been observed in primary astrocytes and astrocytoma cells (Neary, et al, *J Neurochem*, 63:2021–7, 1994; Neary, et al., J Neurochem, 63:490–4, 1994; Rathbone, et al., In Vitro Cell Dev Biol, 28A:529–36, 1992). ATP leads to the induction of a variety of intracellular signaling pathways linked to mitogenic activity, including stimulation of immediate early genes such as c-fos and c-jun, binding of transcription activator protein-1 (AP-1) complex to DNA, and activation of extracellular signal-regulated protein kinase (Bolego, et al., Br J Pharmacol, 121:1692–9, 1997; Chen and Sun, Neurochem Res, 23:543–50, 1998; Priller, et al., Neuroscience, 85:521–5, 1998; Wu, et al., Mol Pharmacol, 53:346, 1998). In the nervous system, glial-specific activation of AP-1 complex, immediate early genes, and ras-MAPK pathway is associated with a primary response of glial cells to perturbation and trauma arising from environmental and genetic etiologies (Segal and Greenberg, Annu Rev Neurosci, 19:463–89, 1996). Activation of these intracellular signaling pathways in glial cells is thought to represent an underlying, adaptive response to neuronal stress and enables glia to mount a neuroprotective response to provide trophic conditioning to neurons from subsequent injury and damage (Segal and Greenberg, Annu Rev Neurosci, 19:463–89, 1996).

Glia often undergo phenotypic changes in response to stress and injury, including proliferation and hypertrophy in a process known a reactive gliosis, which involves upregulation of glial fibrillary acidic protein (GFAP) and elongation of gliotic processes (Eddleston and Mucke, Neuroscience, 54:15–36, 1993; Hatten, et al., Glia, 4:233–43, 1991; Ridet, et al., Trends Neurosci, 20:5707, 1997). Recent work has shown that GFAP-positive, reactive astrocytes are required to protect neurons from extensive cell death in a mechanical injury model of neuronal degeneration in the central nervous system (Bush, et al., Neuron, 23:297–308, 1999). ATP has been shown to increase the expression of GFAP in rat cerebral cortical astrocytes and lengthen astrocytic processes (Abbracchio, et al., Int J Dev Neurosci, 13:685–93, 1995). Similar effects are observed by growth factors such as basic fibroblast growth factor and ciliary neurotrophic factor, which have been shown to confer neuroprotection in a variety of animal models of neurodegeneration (Segal and Greenberg, Annu Rev Neurosci, 19:463–89, 1996).

The following references disclose the compositions of P2Y receptor agonists and/or treatment of eye diseases. U.S. Pat. No. 5,900,407 (Yerxa et al.) discloses a method for the stimulation of tear secretion in a subject in need of treatment. The method comprises administering to the ocular surfaces of the subject a purinergic receptor agonist such as uridine 5'-triphosphate, cytidine 5'-triphosphate, adenosine 5'-triphosphate, or their analogs and derivatives, in an amount effective to stimulate tear fluid secretion. U.S. Pat. No. 5,837,861 (Pendergast et al.) discloses P2Y$_2$ purinergic receptors of dinucleotide polyphosphates having structure of Formula I, wherein X is oxygen, methylene, or difluoromethylene; n=0 or 1; m=0 or 1; n+m=0, 1 or 2; and B and B' are each independently a purine residue or a pyrimidine residue linked through the 9- or 1-position. The compounds are useful in the treatment of chronic obstructive pulmonary diseases, bronchitis, certain pneumonias, cystic fibrosis, sinusitis, and otitis media. U.S. Pat. No. 5,763,447 is directed to a method of preventing or treating pneumonia, including ventilator-associated pneumonia, in a bedridden or immobilized subject in need of such treatment. The method comprises administering to the airways of the patient a purinergic receptor such as uridine 5'-triphosphate (UTP), P$^1$, P$^4$ -di(uridine-5')tetraphosphate, or their analogs, in an amount effective to promote drainage of fluid in the congested airways. WO 99/09998 discloses a method of using uridine 5'-diphosphate and analogs thereof to treat lung disease. The compounds described in the above references ('407, '861, and '447 patents and WO 99/09998), which have purinergic receptor activity, are incorporated herein by reference. Boyer e al., (Br. J. Pharmacol. 118:1959 (1996)) synthesized and tested a series of chain-extended 2-thioether derivatives of adenosine monophosphate (AMP) as agonsists for activation of the phospholipase C-linked P2Y-receptor of turkey erythrocyte membranes, the adenylyl cyclase-linked P2Y-receptor of C6 rat glioma cells, and the cloned human P2U-receptor stably expressed in 1321N1 human astrocytoma cells.

There continues to be a need for methods useful in the treatment retinal degenerations. Such treatment would prevent or reduce the rate of retinal degeneration arising from multiple etiologies. Based on the cellular localization of P2Y receptors in the retina and the signaling pathways of P2Y receptors, we were motivated to explore the utility of P2Y receptor agonists in developing such a treatment.

SUMMARY OF THE INVENTION

The present invention provides a method of preventing or treating retinal degeneration, wherein the retinal degeneration arises from pathophysiological or physical conditions. The method comprises administering to a patient a pharmaceutical composition comprising a P2Y receptor ligand, in an effective amount to activate cell surface P2Y receptors of retinal glial and neuronal cells to mount a neuroprotective response. Methods of administering include intravitreal bolus and sustained administrations, transscleral delivery, topical, oral and systemic administrations, and intraoperative administration.

The pharmaceutical compositions useful in this invention comprise P2Y receptor agonists. P2Y agonists activate $Ca^{2+}$ signaling, mitogen-activated protein kinase signaling, and glial fibrillary acidic protein expression in glial cells of the retina. P2Y agonists include uridine 5'-di- and triphosphate (UDP, UTP) and their analogs (Formulae Ia and Ib), 5'-adenosine monophosphate (AMP) and its analogs, adenosine 5'-di-and triphosphate (ADP, ATP) and their analogs (Formulae IIa and IIb), and cytidine 5'-di-and triphosphate (CDP, CTP) and their analogs (Formulae IIIa and IIIb). P2Y agonists also include dinucleotide polyphosphate compounds of general Formula (IV).

The compounds of the present invention are selective agonists of the P2Y receptors. They are useful in the treatment of neuronal degeneration in the retina in which retinal ganglion cells or photoreceptors are susceptible to death as a result of diseased or physical conditions, including (but not limited to) dry and exudative age-related macular degeneration, Stargardt's disease, Best's disease, and cystoid macular edema, glaucoma, retinitis pigmentosa, retinal detachment, uveitis, photic damage, surgical and traumatic damage, and viral-, bacterial- and toxin-induced retinal degeneration.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

Abbreviations: RPE, retinal pigment epithelium; OS, outer segments; IS, inner segments; ONL, outer nuclear layer; INL, inner nuclear layer; IPL, inner plexiform layer, GCL, ganglion cell layer. Heavy labeling is seen in the RPE and GCL layers of both rabbits and monkeys, and additional labeling is seen in the IS layer of monkeys.

DETAILED DESCRIPTION OF THE INVENTION

The invention provides a method for treating retinal degeneration by providing neuroprotection in the retina. The method comprises administering to a mammal a pharmaceutical composition comprising a therapeutic effective amount of P2Y receptor ligands. The "therapeutic effective amount" used herein means an amount effective to treat retinal degeneration, which is an amount effective to reverse, halt, or delay the degeneration of retinal neurons, or to confer protection of retinal neurons from subsequent damage and degeneration. The preferred method targets retinal glia and neurons to elicit an adaptive response to the activation of the $P2Y_2$ receptor, which is a subtype of the family P2Y receptors, and thus signals a neuroprotective response in the retina. The method administers to a mammal an effective amount of P2Y receptor agonist such that the extracellular concentration of the agonist is sufficient to activate the P2Y receptors on the cell surface in the retina.

Retinal degenerations amenable to treatment disclosed in this invention include retinal degenerative diseases resulting in injury or death of retinal neurons such as photoreceptors and retinal ganglion cells. The retinal degenerative diseases include inherited, acquired, and inflammation induced retinal degenerative diseases. Inherited retinal degenerative diseases include, for example, all forms of macular degeneration such as dry and exudative age-related macular degeneration, Stargardt's disease, Best's disease, glaucoma, retinitis pigmentosa, and optic nerve degeneration. Acquired retinal degenerative diseases, for example, are caused by cystoid macular edema, retinal detachment, photic damage, ischemic retinopathies due to venous or arterial occlusion or other vascular disorders, retinopathies due to trauma, surgery, or penetrating lesions of the eye, and peripheral vitreoretinopathy. Inflammation-induced retinal degenerative diseases are caused by, for example, viral-, bacterial- and toxin-induced retinal degeneration, or uveitis, and may result in optic neuritis. This invention also provides a method for protecting retinal neurons from damage resulting from post-surgical trauma and complications from subsequent exposure to damaging bright light in a protective modality. The method can also be used in conjunction with other therapeutic modalities for treating retinal degenerations, including but not limited to administration with growth factors, neurotrophins, cytokines, ribozymes, anti-inflammatory agents, antibiotics, anti-viral agents, and gene therapy.

This invention provides that $P2Y_2$ receptors are localized to multiple cell types in the retina, and are heavily expressed in retinal ganglion cells, astrocytes, Müller cells, photoreceptors, and retinal pigment epithelium. Applicants believe that the activation of P2Y receptors in Müller cells causes activation and upregulation of glial fibrillary acidic protein (GFAP) throughout the radial processes of Müller cells, which plays a significant role in the observed $P2Y_2$ receptor-induced protection of retinal neurons.

This invention provides a method of using a pharmaceutical composition comprising P2Y receptor agonists for the treatment of a variety of retinopathies. P2Y agonists include nucleoside mono-, di-, and triphosphates and dinucleoside polyphosphates. Nucleoside monophosphates useful in this invention include adenosine 5'-monophosphate (AMP) and its derivatives such as 2-thioether-substituted AMP, e.g., 2-hexylthio AMP (*Br. J. Pharmacol.* 118:1959 (1996)). Nucleoside di-and triphosphates useful in this application include uridine 5'-di- and triphosphate (UDP and UTP) and their analogs of general formulae Ia and Ib; adenosine 5'-di- and triphosphate (ADP and ATP) and their analogs of general formulae IIa and IIb; and cytosine 5'-di- and triphosphate (CDP and CTP) and their analogs of general formulae IIIa and IIIb; and dinucleoside polyphosphates of general formula IV.

UDP and its analogs are depicted by general formula Ia:

Formula Ia wherein:
$X_1$, and $X_2$ are each independently either a O* or S*;
Y is H or OH;
$R_1$ is selected from the group consisting of O, imido, methylene, and dihalomethylene (e.g., dichloromethylene, difluoromethylene);
$R_2$ is selected from the group consisting of H, halogen, alkyl, substituted alkyl, alkoxyl, nitro and azido;
$R_3$ is selected from the group consisting of nothing, H, alkyl, acyl (including arylacyl), and arylalkyl; and
$R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring. As used herein, the term "alkyl" refers to $C_{10}$ inclusive, linear, branched, or cyclic, saturated or unsaturated (i.e., alkenyl and alkynyl) hydrocarbon chains, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl and optionally substituted arylalkenyl and arylalkyny groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Examples of aryl groups include cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_{1-10}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to aryloxy such as phenyloxyl, and alkyl, halo, or alkoxyl substituted aryloxyl. As used herein, the terms "substituted alkyl" and "substituted aryl" include alkyl and aryl groups, as defined herein, in which one or more atoms or functional groups of the aryl or alkyl group are replaced with another atom or functional group, for example, halogen, aryl, alkyl, alkoxy, hydroxy, nitro, amino, alkylamino, dialkylamino, sulfate, and mercapto. The terms "halo," "halide," or "halogen" as used herein refer to fluoro, chloro, bromo, and iodo groups.

Compounds illustrative of the compounds of Formula (Ia) include those disclosed in WO 99/09998; the reference is incorporated herein by reference. Formula Ia compounds, for example, include: uridine 5'-diphosphate (UDP); uridine 5'-O-(2-thiodiphosphate)(UDPβS); 5-bromouridine 5'-diphosphate (5-BrUDP); 5-(1-phenylethynyl)-uridine 5'-diphosphate (5-(1-phenylethynyl)UDP); 5-methyluridine 5'-diphosphate (5-methylIUDP); 4-hexylthiouridine 5'-diphosphate (4-hexylthioUDP); 4-mercaptouridine 5'-diphosphate (4-mercaptoUDP); 4-methoxyuridine 5'-diphosphate (4-methoxyUDP); 4-(N-morpholino)uridine 5'-diphosphate (4-(N-morpholino)UDP; 4-hexyloxyuridine 5'-diphosphate (4-hexyloxyUDP); N,N-dimethylcytidine 5'-diphosphate (N,N-dimethylCDP); N-hexylcytidine 5'-diphosphate (N-hexylCDP); and N-cyclopentylcytidine 5'-diphosphate (N-cyclopentylCDP).

Preferred compounds of Formula Ia include UDP and UDPβS and 4-thio UDP. Certain compounds of Formula Ia (e.g., UDP, dUDP, UDPβS, and 4-mercaptoUDP) are known and may be made in accordance with known procedures or variations thereof, which will be apparent to those skilled in the art. For example, the identification and preparation of certain thiophosphate analogues of nucleoside diphosphates (such as UTP-β-S) are set forth in U.S. Pat. No. 3,846,402 (Eckstein et al.), and in R. S. Goody and F. Eckstein, *J. Am. Chem. Soc.* 93: 6252–6257 (1971). Alternatively, UDP, and other analogs thereof are also commercially available from vendors such as Sigma (St. Louis, Mo.) and Pharmacia (Uppsala, Sweden).

UTP and its analogs are depicted by general formula Ib;

Formula Ib wherein:

$X_1$, $X_2$ and $X_3$ are each independently either O* or S*,

Y is H or OH;

$R_1$, $R_2$, $R_3$ and $R_4$ are defined as in Formula Ia

Preferably, $X_2$ and $X_3$ are O*, $R_1$ is oxygen or imido, and $R_2$ is H. Particularly preferred compounds of Formula Ib include uridine 5'-triphosphate (UTP) and uridine 5'-O-(3-thiotriphosphate) (UTPγS).

ADP and its analogs are depicted by general Formula IIa:

Formula IIa wherein:

$R_1$, $X_1$, $X_2$ and Y are defined as in Formula Ia;

Z is H, Cl, or SR, wherein R is alkyl ($C_1$–$C_{20}$, saturated or unsaturated);

$R_3$ and $R_4$ are H while $R_2$ is nothing and there is a double bond between N-1 and C-6 (adenine), or

$R_3$ and $R_4$ are H while $R_2$ is nothing and Z is SR, or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,N6-ethenoadenine).

Particularly preferred compounds of Formula IIa include 5'-adenosine diphosphate (ADP) and 2-methyl-SADP.

ATP and its analogs are depicted by general Formula IIb:

Formula IIb wherein:

$R_1$, $X_1$, $X_2$, $X_3$ and Y are defined as in Formula Ib, and $R_2$, $R_3$, $R_4$ and Z are defined as in Formula IIIa.

CDP and its analogs are depicted by general Formula IIIa:

Formula IIIa wherein:

$R_1$, $X_1$, $X_2$ and Y are defined as in Formula Ia;

$R_5$ and $R_6$ are H while $R_7$ is nothing and there is a double bond between N-3 and C-4 (cytosine), or $R_5$ and $R_6$ taken together are —CH=CH—, forming a ring from N-3 to NA with a double bond between NA and C-4 (3,$N^4$-ethenocytosine), optionally the hydrogen of the 4- or 5-position of the etheno ring is substituted with alkyl, substituted alkyl, aryl, substituted aryl (heteroaryl, etc.), alkoxyl, nitro, halogen, or azido.

$Z$=OH or $N_3$;
$Z'$=OH or $N_3$;
$Y$=H or OH; and
$Y'$=H or OH.

The ribosyl moieties are in the D-configuration, as shown, but may be L-, or D- and L-. The D- configuration is preferred.

A preferred compound of Formula IV includes Formula IVa:

Formula IVa

CTP and its analogs are depicted by general Formula IIIb:

Formula IIIb wherein:
$R_1$, $X_1$, $X_2$, $X_3$ and Y are defined as in Formula Ib, and $R_5$, $R_6$ and $R_7$ are defined as in Formula IIIa.

Preferred compounds of Formula IIIb include cytidine 5'-triphosphate (CTP) and 4-nitrophenyl ethenocytidine 5'-triphosphate.

For simplicity, Formulas I, II, and III, herein illustrate the active compounds in the naturally occurring D-configuration, but the present invention also encompasses compounds in the L-configuration, and mixtures of compounds in the D- and L-configurations, unless otherwise specified. The naturally occurring D-configuration is preferred.

Dinucleoside polyphosphates are depicted by general Formula IV:

wherein:
X is oxygen, methylene, difluoromethylene, imido;
n=0, 1 or 2;
m=0, 1 or 2;
n+m=0, 1, 2, 3 or 4;
B and B' are each independently a purine residue or a pyrimidine residue linked through the 9- or 1-position, respectively;

wherein:
X=O;
n+m=1 or 2;
Z, Z', Y and Y'=OH;
B and B' are uracil, thymine, cytosine, guanine, adenine, xanthine, hypoxanthine or as defined in Formulas V and VI; or
X=O;
n+m=3 or 4;
Z, Z', Y and Y'=OH;
B=uracil;
B' is uracil, thymine, cytosine, guanine, adenine, xanthine, hypoxanthine or as defined in Formulas V and VI; or
X=O;
n+m=1 or 2;
Z, Y and Z'=OH;
Y'=H,
B=uracil;
B' is uracil, thymine, cytosine, guanine, adenine, xanthine, hypoxanthine or as defined in Formulas V and VI; or
X=O;
n+m=0, 1 or 2;
Z and Y=OH;
Z'=$N_3$;
Y'=H;
B=uracil;
B'=thymine; or
X=O;
n+m=0, 1 or 2;
Z and Z'=$N_3$;
Y and Y'=H;
B and B'=thymine; or
X=$CH_2$, $CF_2$ or NH;
n and m=1;
Z, Z', Y and Y'=OH;
B and B' are uracil, thymine, cytosine, guanine, adenine, xanthine, hypoxanthine or as defined in Formulas V and VI:

Formula V

Formula VI wherein

R$_1$ is hydrogen, C$_{1-8}$alkyl, C$_{3-6}$, cycloalkyl, phenyl, or phenyloxy; wherein at least one hydrogen of said C$_{1-8}$alkyl, phenyl, phenyloxy, is optionally substituted with a moiety selected from the group consisting of halogen, hydroxy, C$_{1-4}$alkoxy, C$_{1-4}$alkyl, C$_{6-10}$aryl, carboxy, cyano, nitro, sulfonamido, sulfonate, phosphate, sulfonic acid, amino, C$_{1-4}$ alkylamino, di-C$_{1-4}$ alkylamino wherein said alkyl groups are optionally linked to form a heterocycle, ω-A(alkyl)CONH(alkyl)-, and ω-A(alkyl)NHCO(alkyl)-, wherein A is amino, mercapto, hydroxy or carboxyl;

R$_2$ is O or is absent; or

R$_1$ and R$_2$ taken together form a 5-membered fused imidazole ring optionally substituted on the 4- or 5- positions of the etheno moiety with C$_{1-4}$alkyl, phenyl or phenyloxy, wherein at least one hydrogen of said C$_{1-4}$alkyl, phenyl, phenyloxy, is optionally substituted with a moiety selected from the group consisting of halogen, hydroxy, C$_{1-4}$alkoxy, C$_{1-4}$alkyl, C$_{6-10}$aryl, C$_{7-12}$arylalkyl, carboxy, cyano, nitro, sulfonamido, sulfonate, phosphate, sulfonic acid, amino, C$_{1-4}$ alkylamino, and di-C$_{1-4}$ alkylamino wherein said dialkyl groups are optionally linked to form a heterocycle; and R$_3$ is hydrogen, NH$_2$, C$_{1-8}$alkyl, C$_{3-6}$ cycloalkyl, phenyl; or phenyloxy; wherein at least one hydrogen of said NH$_2$, C$_{1-8}$ alkyl, phenyl, or phenyloxy, is optionally substituted with a moiety selected from the group consisting of halogen, hydroxy, C$_{1-4}$alkoxy, C$_{6-10}$aryl C$_{7-12}$arylalkyl, C$_{1-4}$alkoxy, C$_{7-12}$arylalkyloxy, C$_{1-4}$alkylthio, phenylthio, C$_{7-12}$arylalkylthio, carboxy, cyano, nitro, sulfonamido, sulfonate, phosphate, sulfonic acid, amino, C$_{1-4}$ alkylamino, phenylamino, C$_{7-12}$arylalkyamino, di-C$_{1-4}$ alkyl amino wherein said dialkyl groups are optionally linked to form a heterocycle, ω-A(alkyl)CONH(alkyl)B-, and ω-A(alkyl)NHCO(alkyl)B-, wherein A and B are independently amino, mercapto, hydroxy or carboxyl.

The substituted derivatives of adenine (Formula V) include adenine 1-oxide; 1,N6-(4- or 5-substituted etheno) adenine; 6-substituted adenine; or 8-substituted aminoadenine, [6-aminohexyl]carbamoylmethyl-adenine; and ω-acylated- amino(hydroxy, thiol and carboxy)alkyl(C$_{2-10}$)-adenine, wherein the acyl group is chosen from among, but not limited to, acetyl, triflororoacetyl, benzoyl, substituted-benzoyl, etc., or the carboxylic moiety is present as its ester or amide derivative, for example, the ethyl or methyl ester or its methyl, ethyl or benzamido derivative.

B and B', can also be a pyrimidine with the general formula of Formula VI, linked through the 1- position to ribosyl residue:

wherein:

R$_4$ is hydrogen, hydroxy, mercapto, amino, cyano, C$_{7-12}$arylalkoxy, C$_{1-6}$ alkylthio, C$_{1-6}$ alkoxy, C$_{1-6}$ alkylamino or diC$_{1-4}$alkylamino, wherein the alkyl groups are optionally linked to form a heterocycle;

R$_5$ is hydrogen, acetyl, benzoyl, C$_{1-6}$ alkyl, phenyloxy, C$_{1-5}$ alkanoyl, aroyl, or sulphonate;

R$_6$ is hydroxy, mercapto, C$_{1-4}$alkoxy, C$_{7-12}$arylalkoxy, C$_{1-6}$alkylthio, amino, S-phenyl, C$_{1-5}$ disubstituted amino, triazolyl, C$_{1-6}$alkylamino, or di-C$_{1-4}$alkylamino wherein said dialkyl groups are optionally linked to form a heterocycle or linked to N$^3$ to form a substituted ring; or R$_5$ and R$_6$ taken together form a 5-membered fused imidazole ring between positions 3 and 4 of the pyrimidine ring and form a 3,N$^4$-ethenocytosine derivative, wherein said etheno moiety is optionally substituted on the 4 or 5- positions with C$_{1-4}$ alkyl; phenyl; or phenyloxy; wherein at least one hydrogen of said C$_{1-4}$alkyl; phenyl or phenyloxy is optionally substituted with a moiety selected from the group consisting of halogen, hydroxy, C$_{1-4}$alkoxy, C$_{1-4}$alkyl, C$_{6-10}$aryl C$_{7-12}$arylalkyl, carboxy, cyano, nitro, sulfonamido, sulfonate, phosphate, sulfonic acid, amino, C$_{1-4}$ alkylamino, and di- C$_{1-4}$ alkylamino wherein said dialkyl groups are optionally linked to form a heterocycle;

R$_7$ is hydrogen, hydroxy, cyano, nitro, or C$_{2-8}$alkenyl; wherein said alkenyl moiety is optionally linked through an oxygen to form a ring, wherein at least one hydrogen of said alkenyl moiety on the carbon adjacent to said oxygen is optionally substituted with C$_{1-6}$alkyl, phenyl, substituted C$_{2-8}$alkynyl, halogen, substituted C$_{1-4}$alkyl, CF$_3$, C$_{2-3}$ alkenyl, C$_{2-3}$ alkynyl, allylamino, bromovinyl, ethyl propenoate, or propenoic acid; or R$_6$ and R$_7$ together form a 5 or 6-membered saturated or unsaturated ring bonded through N or O at R$_6$ such ring optionally contains substituents that themselves contain functionalities; provided that when R$_8$ is amino or substituted amino, R$_7$ is hydrogen; and R$_8$ is hydrogen, amino or di-C$_{1-4}$alkylamino, C$_{1-4}$alkoxy, C$_{7-12}$arylalkoxy, C$_{1-4}$alkylthio, C$_{7-12}$arylalkylthio, carboxamidomethyl, carboxymethyl, methoxy, methylthio, phenoxy or phenylthio.

In the general structure of Formulae I, II, III, V, and VI above, the dotted lines in the 2- to 6- positions are intended to indicate the presence of single or double bonds in these positions; the relative positions of the double or single bonds being determined by whether the R$_4$, R$_5$ and R$_6$ substituents are capable of keto-enol tautomerism.

In the general structures of Formula V and VI above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

Preferred dinucleoside polyphosphate compounds useful in this invention are $P^1$, $P^4$-di (urdine-5')-tetraphosphate, $dUP_4U$, $U_2P_3$, $U_2P_5$, $dCP_4U$, $CP_4U$, $IP_5I$, $AP_4A$, $CP_3U$, $UP_3A$ and $A_2P_3$.

Some compounds of Formula I, II and III can be made by methods known those skilled in the art; some compounds are commercially available, for example, from Sigma Chemical Co. (St. Louis, Mo. 63178). Compounds of Formulae Ia (UDP and its analogs) can be prepared according to WO 99/09998. Compounds of Formulae Ib, IIb and IIIb (UTP, ATP, CTP and their analogs) can be prepared according to U.S. Pat. No. 5,763,447. Compounds of Formula IV can be made in accordance with known procedures described by Zamecnik, et al., *Proc. Natl. Acad. Sci.* USA 89, 838–42 (1981); and Ng and Orgel, *Nucleic Acids Res.* 15:3572–80 (1987), Pendergast et al., U.S. Pat. No. 5,837,861, or variations thereof.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$(wherein X is $C_{1-4}$). Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies which may be employed to prepare non-toxic pharmaceutically acceptable salts and acylated prodrugs of the compounds.

The pharmaceutical compositions can be administered by topical, systemic, subscleral, transscleral, or intravitreal delivery such that the extracellular concentration of a $P2Y_2$ agonist is elevated to activate cell surface P2Y receptors in the retina. Preferred methods of delivery are intravitreal delivery and transscleral delivery. Intravitreal delivery may include single or multiple intravitreal injections, or via an implantable intravitreal device that releases P2Y agonists in a sustained capacity. Intravitreal delivery may also include delivery during surgical manipulations in treatment for retinal detachments, diabetic retinopathy, or macular degenerations as either an adjunct to the intraocular irrigation solution or applied directly to the vitreous during the surgical procedure.

Minimally invasive transscleral delivery can be used to deliver an effective amount of the active compounds to retina with negligible systemic absorption. Transscleral delivery utilizes the sclera's large and accessible surface area, high degree of hydration which renders it conductive to water-soluble substances, hypocellularity with an attendant paucity of protcolytic enzymes and protein-binding site, and permeability that does not appreciably decline with age. An osmotic pump loaded with active compounds can be implanted in a subject so that the active compounds are transsclerally delivered to retina in a slow-release mode. (Ambati, et al., *Invest. Ophthalmol. Vis. Sci.,* 41: 1186–91 (2000))

The active compounds may also be administered topically by administering the active compounds to the eyes of a patient by any suitable means, but are preferably administered by a liquid or gel suspension of the active compound in the form of drops, spray or gel. Alternatively, the active compounds may be applied to the eye via liposomes. Further, the active compounds may be infused into the tear film via a pump-catheter system. Another embodiment of the present invention involves the active compound contained within a continuous or selective-release device, for example, membranes employed in the QCUSERT™ System (polymeric ocular inserts for the administration of drugs. Alza Corp., Palo Alto, Calif.), or in the VITRASERT® System (intra-vitreal implant for the gradual release of pharmaceuticals for the treatment of eye conditions, Bausch & Lomb, Claremont, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface.

The active compounds may be administered systemically to eyes. The term systemic as used herein includes subcutaneous injection; intravenous, intramuscular, intraesternal injection; infusion; inhalation, transdermal administration, oral administration; and intra-operative instillation.

One systemic method involves an aerosol suspension of respirable particles comprising the active compound, which the subject inhales. The active compound would be absorbed into the bloodstream via the lungs, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another method of systemically administering the active compounds to the eyes of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

The active compounds may also be systemically administered to eyes through absorption by the skin using transdermal patches or pads. The active compounds are absorbed into the bloodstream through the skin. Plasma concentration of the active compounds can be controlled by using patches containing different concentrations of active compounds.

Other methods of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs. Additional means of systemic administration of the active compound to the eyes of the subject would involve a suppository form of the active compound, such that a therapeutically effective amount of the compound reaches the eyes via systemic absorption and circulation.

Further means of systemic administration of the active compound involve direct intra-operative instillation of a gel, cream, or liquid suspension form of a therapeutically effective amount of the active compound.

For topical application, the solution containing the active compound may contain a physiologically compatible vehicle, as those skilled in the ophthalmic art can select, using conventional criteria. The vehicles may be selected from the known ophthalmic vehicles which a include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

For systemic administration such as injection and infusion, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The pharmaceutical utility of P2Y agonist compounds of this invention are indicated by the inositol phosphate assay for P2Y activity. This widely used assay, as described in E. Lazarowski, et al., Brit. *J. Pharm.* 116, 1619–27 (1995), relies on the measurement of inositol phosphate formation as a measurement of activity of compounds activating receptors linked via G-proteins to phospholipase C.

The present invention provides that activation of P2Y purinergic receptors in glial cells by agonists enhances the survival of neurons in vivo. The present invention describes the utility of agonist-induced activation of purinergic receptors in glia of the sensory nervous system in mounting a neuroprotective response by addressing a plurality of diseases under which a therapeutic modality is clinically beneficial.

The invention is illustrated further by the following examples which are not to be construed as limiting the invention in scope or spirit to the specific procedures described in them.

EXAMPLES

Example 1

Localization of P2Y Receptor Gene Expression in Rabbit and Primate Retina

Tissues. Albino rabbit and monkey retina were prepared following enucleation of the eye, fixation, and cryopreservation. Tissue were cryosectioned into cross-sections across the retina, retinal pigment epithelium, and choroid into 5 μm thick sections and mounted onto glass slides for in situ hybridization with sense and anti-sense oligonucleotide probes specifically designed against regions of the $P2Y_2$ mRNA. Tissues were also counter stained with hemotoxylin and eosin (H&E) to evaluate the quality and orientation of study tissues. Examination of H&E slides a indicated that all tissues were suitable for ISH.

Riboprobe Synthesis. A PCR product containing nucleotides 253–651 from a human $P2Y_2$-R cDNA was obtained from a sponsor. $P2Y_2$-R nucleotides 272–627 were reamplified with $P2Y_2$ primers (forward primer sequence: 5' AGGAGATGTGTTGGGCAGCAGTGAGGAC 3', SEQ ID NO:1; reverse primer sequence: reverse 5' ACCAGGGTTTTCTGGCCAACCTGTGACT 3' SEQ ID NO:2) designed to eliminate flanking plasmid sequences and incorporate either an upstream T3 promotor or a downstream T7 promotor. The resulting PCR products were used to synthesize digoxigenin-labeled riboprobes by in vitro transcription (IVT). Antisense and sense riboprobes were synthesized using T7 and T3 RNA polymerases, respectively, in the presence of digoxigenin-11-UTP (Boehringer-Mannheim) using a MEGAscript, or MAXIscript IVT kit (Ambion) according to the manufacturer. Following IVT, template DNA was degraded with DNase-1, and unincorporated digoxigenin was removed by ultrafiltration. Riboprobe integrity was assessed by electrophoresis through a denaturing polyacrylamide gel. Apparent molecular size was estimated by comparison with the electrophoretic mobility of a 100–1000 base pair RNA ladder (Ambion). Probe yield and labeling was evaluated by blot immunochemistry. Riboprobes were dispensed in 5 µL aliquots and stored at −80° C. until used for ISH.

In Situ hybridization. Frozen tissues were cut into 5 µm sections, mounted on SuperFrost Plus slides (Fisher Scientific), and post-fixed for 15 minutes in 4% paraformaldehyde in PBS at pH 7.4. Sections were prehybridized in the absence of probe, then incubated overnight in hybridization buffer containing 400 ng/mL of either antisense or sense probe. Following hybridization, slides were subjected to a series of post-hybridization stringency washes to reduce nonspecific staining. Hybridization was visualized by immunohistochemistry using alkaline phosphatase-conjugated anti-digoxigenin Fab and nitroblue tetrazolium chloride-bromochloroindolyl phosphate (Boehringer-Mannheim) according to the manufacturer. Tissue sections were counter stained with nuclear fast red. Negative controls included retinal tissues stained with the sense $P2Y_2$-R probe.

Figure 1:
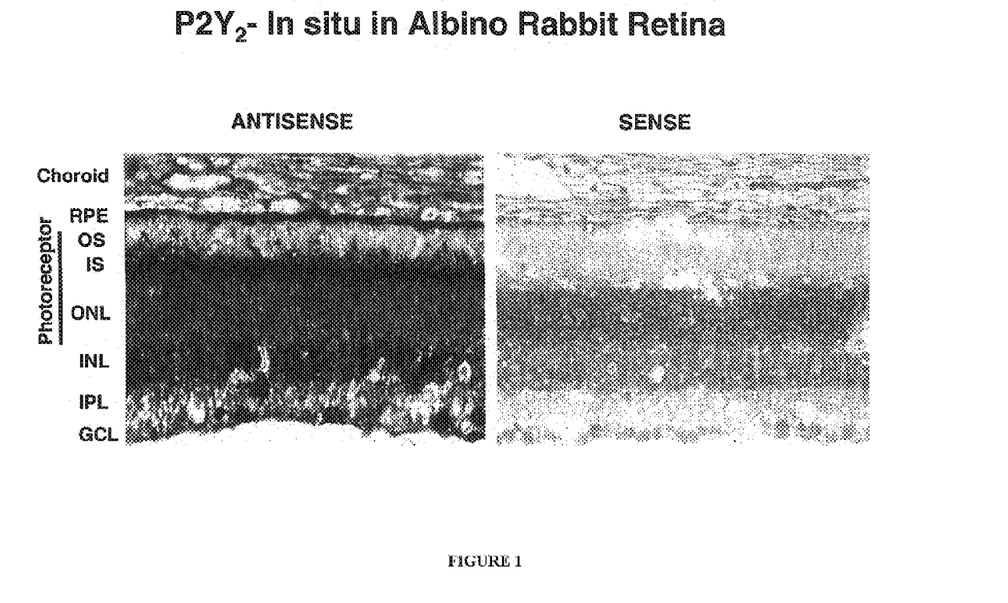
FIG. 1 shows in In situ localization of P2Y$_2$ mRNA in adult rabbit retina by DIG-labeling of anti-sense probe (left) and sense probe (right).
Figure 2:
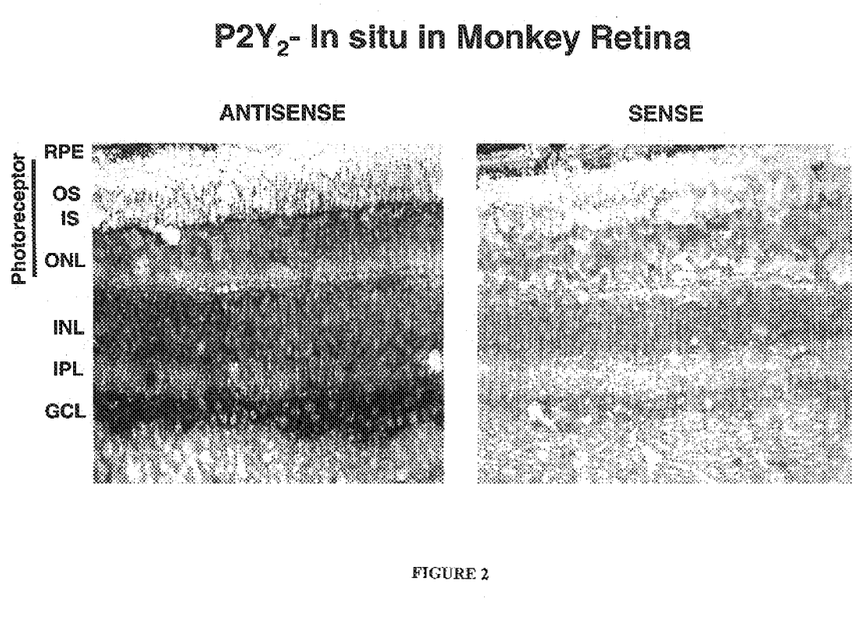
FIG. 2 shows in In situ localization of P2Y$_2$ mRNA in monkey retina by DIG-labeling of anti-sense probe (left) and sense probe (right).

Results. The two pairs of slides show the sense and antisense results for the rabbit (FIG. 1) and monkey tissues (FIG. 2). Both tissues show positive staining using the antisense probe (FIGS. 1 and 2, left), but negative staining using the control sense probe (FIGS. 1, 2, right). These results demonstrate that both rabbit and monkey retina contain the message for the $P2Y_2$ receptors. The cellular localization of the antisense probe demonstrates punctate $P2Y_2$ expression along the inner limiting membrane, consistent with localization in retinal astroctyes whose cell bodies are located primarily in this layer. Cell body staining was also observed in the ganglion cell layer and in a subset of cell in the inner nuclear layer, consistent with the presence of $P2Y_2$ in ganglion and Müller cells. Additional staining is seen through the outer limiting membrane and may reflect either cytoplasmic staining of Müllier cell microvilli or photoreceptor inner segments. Finally, strong staining is seen along the retinal pigment epithelium (RPE). Thus $P2Y_2$ expression is demonstrated in retinal neurons and glia.

Example 2

Protection of Photoreceptors from the Damaging Effect of Constant Light

Animal models. Photoreceptors of albino Sprague-Dawley rats are susceptible to damage as a result of exposure approximately 4 days of constant bright light. The light-induced photoreceptor degeneration in Sprague-Dawley rats is a widely used animal model for retinal degeneration in humans following exposure to toxic levels of bright light, or in diseased conditions (LaVail, et al., *Proc Natl Acad. Sci.*, 89:11249–11253, 1992). This model is used to test the ability of $P2Y_2$ receptor to protect photoreceptors from degeneration caused by exposure to constant bright light.

Experimental design. Sprague-Dawley rats are brought in at∼10 weeks of age and housed under 12 hour cyclic light/dark illumination with an in-cage illuminance of ∼20 ft-cd. Two days prior to exposure to bright light, animals are injected with P2Y receptor agonists, such as ADP, UDP, UTP or $dCP_4U$, and returned to normal cyclic lighting conditions, at which point animals are then housed under constant bright light (∼175 ft-cd) for 84 hours. After 84 hours of constant bright illumination, animals are then returned to normal, cyclic lighting conditions for two weeks prior to sacrifice. To assess for retinal function, scotopic and photopic electroretinograms (ERGs) are performed one week prior and exposure to bright light, and just prior to sacrifice. ERGs provide a functional measure of electrical activity originating across the retina in response to exposure to brief flashes of light, and represent a relatively non-invasive measure of photoreceptor function and integrity, Following sacrifice, eyes are enucleated and processed for paraffin sections and stained with hemotoxylin and eosin to resolve the histological features of the retina. The histological analysis provides morphological information of photoreceptors and other parts of the retina at a cellular level. Animals are treated in one eye with P2Y agonist and in the contralateral eye with vehicle (control) buffer.

Results. Animals treated with P2Y receptor agonists and controls are examined for neutroprotetion of photoreceptors. Positive neuroprotection results are indicated by the following. The thickness of the entire photoreceptor layer (consisting of the outer nuclear layer, inner segments and outer segments) is significantly larger in eyes treated with P2Y agonists. Also, thickness of the outer nuclear layer (consisting of nuclei of photoreceptors) is larger, indicating a greater number of surviving photoreceptors in response to treatment with P2Y receptor agonists. Scotopic a-wave amplitudes (representing photoreceptor function) and b-wave amplitudes (representing inner retinal contributions) are larger in eyes having positive neuroprotection results. The histological and electrophysiological results demonstrate the effect of treatment.

What is claimed is:

1. A method of treating a retinal degenerative disease comprising:
   administering to a patient a pharmaceutical composition comprising a therapeutically effective amount of a P2Y receptor agonist compound, wherein said amount is effective to increase the extracellular concentration of said agonist in a retina such that cell surface P2Y receptors of retinal glial cells and neuronal cells are activated to mount a neuroprotective response, wherein said retinal degenerative disease is primarily a degenerative disease and does not have a retinal edematous component.

2. The method according to claim 1, wherein said P2Y receptor agonist compound is a dinucleoside polyphosphate selected from the group consisting of compounds of Formula IV and pharmaceutically acceptable salts thereof:

Formula IV wherein:
X is oxygen, methylene, difluoromethylene, or imido;
n=0, 1 or 2;
m=0, 1 or 2;
n+m=0, 1, 2, 3 or 4;
B and B' are each independently a purine residue or a pyrimidine residue linked through the 9- or 1-position, respectively;
Z=OH or $N_3$;
Z'=OH or $N_3$;
Y=H or OH; and
Y'=H or OH.

3. The method according to claim 2, wherein said dinucleoside polyphosphate is selected from the group consisting of compounds of Formula IVa and pharmaceutically acceptable salts thereof:

Formula IVa wherein:

X=O;

n+m=1 or 2;

Z, Z', Y and Y'=OH;

B and B' are uracil, thymine, cytosine, guanine, adenine, xanthine, hypoxanthine, or as defined in Formulas V and VI; or

X=O;

n+m=3 or 4;

Z, Z', Y and Y'=OH;

B=uracil;

B' is uracil, thymine, cytosine, guanine, adenine, xanthine, hypoxanthine or as defined in Formulas V and VI; or

X=O;

n+m=1 or 2;

Z, Y and Z'=OH;

Y'=H;

B=uracil;

B' is uracil, thymine, cytosine, guanine, adenine, xanthine, hypoxanthine or as defined in Formulas V and VI; or

X=O;

n+m=0, 1 or 2;

Z and Y=OH;

Z'=N$_3$;

Y'=H;

B=uracil;

B'=thymine; or

X=O;

n+m=0, 1 or 2;

Z and Z'=N$_3$;

Y and Y'=H;

B and B'=thymine; or

X=CH$_2$, CF$_2$ or NH;

n and m=1;

Z, Z', Y and Y'=OH;

B and B' are uracil, thymine, cytosine, guanine, adenine, xanthine, hypoxanthine or as defined in Formulas V and VI;

Formula V wherein $R_1$ is hydrogen; $C_{1-8}$alkyl; phenyl; or phenyloxy, wherein at least one hydrogen of said $C_{1-8}$alkyl, phenyl, phenyloxy, is optionally substituted with a moiety selected from the group consisting of halogen, hydroxy, $C_{1-4}$alkoxy, $C_{1-4}$alkyl, $C_{6-10}$aryl, carboxy, cyano, nitro, sulfonamido, sulfonate, phosphate, sulfonic acid, amino, $C_{1-4}$ alkylamino, di-$C_{1-4}$ alkylamino wherein said alkyl groups are optionally linked to form a heterocycle, ω-A($C_{1-6}$alkyl)CONH($C_{1-6}$alkyl), and ωA($C_{1-6}$alky)NHCO($C_{1-6}$alkyl)-, wherein A is amino, mercapto, hydroxy or carboxyl;

$R_2$ is O or is absent; or $R_1$ and $R_2$ taken together form a 5-membered fused imidazole ring optionally substituted on the 4- or 5-positions of the etheno moiety with $C_{1-4}$alkyl, phenyl or phenyloxy, wherein at least one hydrogen of said $C_{1-4}$alkyl, phenyl, phenyloxy, is optionally substituted with a moiety selected from the group consisting of halogen, hydroxy, $C_{1-4}$alkoxy, $C_{1-4}$alkyl, $C_{6-10}$aryl, $C_{7-12}$arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle; and $R_3$ is hydrogen, NH$_2$, $C_{1-8}$alkyl, phenyl, or phenyloxy; wherein at least one hydrogen of said NH$_2$, $C_{1-8}$ alkyl, phenyl, or phenyloxy, is optionally substituted with a moiety selected from the group consisting of halogen, hydroxy, $C_{1-4}$alkyl, $C_{6-10}$aryl, $C_{7-12}$arylalkyl, $C_{1-4}$alkoxy, $C_{7-12}$arylalkyloxy; $C_{1-4}$alkylthio, phenylthio, $C_{7-12}$arylalkylthio, carboxy, cyano, nitro, sulfonamido, sulfonate, phosphate, sulfonic acid, amino, $C_{1-4}$ alkylamino, phenylamino, $C_{7-12}$arylalkyamino, di-$C_{1-4}$ alkyl amino wherein said dialkyl groups are optionally linked to form a heterocycle, ω-A($C_{1-6}$alkyl)CONH($C_{1-6}$alkyl)B-, and ω-A($C_{1-6}$alkyl)NHCO($C_{1-6}$alkyl)B-, wherein A and B are independently amino, mercapto, hydroxy or carboxyl;

Formula VI wherein:

R$_4$ is hydrogen, hydroxy, mercapto, amino, cyano, C$_{7-12}$arylalkoxy, C$_{1-6}$ alkylthio, C$_{1-6}$ alkoxy, C$_{1-6}$ alkylamino or diC$_{1-4}$alkylamino, wherein the alkyl groups are optionally linked to form a heterocycle;

R$_5$ is hydrogen, acetyl, benzoyl, C$_{1-6}$ alkyl, phenyloxy, C$_{1-5}$ alkanoyl, aroyl, or sulphonate;

R$_6$ is hydroxy, mercapto, C$_{1-4}$alkoxy, C$_{7-12}$arylalkoxy, C$_{1-6}$alkylthio, amino, C$_{1-5}$ disubstituted amino, triazolyl, C$_{1-4}$alkylamino, or di-C$_{1-4}$alkylamino wherein said dialkyl groups are optionally linked to form a heterocycle or linked to N$^3$ to form a substituted ring; or R$_5$ and R$_6$ taken together form a 5-membered fused imidazole ring between positions 3 and 4 of the pyrimidine ring and form a 3,N$^4$-ethenocytosine derivative, wherein said etheno moiety is optionally substituted on the 4- or 5- positions with C$_{1-4}$ alkyl; phenyl; or phenyloxy; wherein at least one hydrogen of said C$_{1-4}$alkyl; phenyl or phenyloxy is optionally substituted with a moiety selected from the group consisting of halogen, hydroxy, C$_{1-4}$alkoxy, C$_{1-4}$alkyl, C$_{6-12}$aryl, C$_{7-12}$arylalkyl, carboxy, cyano, nitro, sulfonamido, sulfonate, phosphate, sulfonic acid, amino, C$_{1-4}$ alkylamino, and di- C$_{1-4}$ alkylamino wherein said dialkyl groups are optionally linked to form a heterocycle;

R$_7$ is hydrogen, hydroxy, cyano, nitro, or C$_{2-8}$alkenyl; wherein said alkenyl moiety is optionally linked through an oxygen to form a ring, wherein at least one hydrogen of said alkenyl moiety on the carbon adjacent to said oxygen is optionally substituted with C$_{1-6}$alkyl, phenyl, substituted C$_{2-8}$alkynyl, halogen, substituted C$_{1-4}$alkyl, CF$_3$, C$_{2-3}$ alkenyl, C$_{2-3}$ alkynyl, allylamino, bromovinyl, ethyl propenoate, or propenoic acid; or R$_6$ and R$_7$ together form a 5 or 6-membered saturated or unsaturated ring bonded through N or O at R$_6$, such ring optionally contains substituents that themselves contain functionalities; provided that when R$_8$ is amino or substituted amino, R$_7$ is hydrogen; and R$_8$ is hydrogen, amino or di-C$_{1-4}$alkylamino, C$_{1-4}$alkoxy, C$_{7-12}$arylalkoxy, C$_{1-4}$alkylthio, C$_{7-12}$arylalkylthio, carboxamidomethyl, carboxymethyl, methoxy, methylthio, phenoxy or phenylthio.

4. The method according to claim 3, wherein said compound of Formula IVa is U$_2$P$_4$, dUP$_4$U, U$_2$P$_3$, U$_2$P$_5$, dCP$_4$U, CP$_4$U, IP$_5$I, AP$_4$A, CP$_3$U, UP$_3$A, or A$_2$P$_3$.

5. The method according to claim 1, wherein said compound is administered to a patient by an intravitreal delivery.

6. The method according to claim 1, wherein said compound is administered to a patient by a transscleral delivery.

7. The method according to claim 1, wherein said compound is administered to a patient by topical administration.

8. The method according to claim 7, wherein said topical administration is via a carrier vehicle selected from the group consisting of drops of liquid, liquid washes, gels, ointments, sprays and liposomes.

9. The method according to claim 7, wherein said topical administration comprises infusion of said compound to an ocular surface via a device selected from the group consisting of a pump-catheter system, a continuous or selective release device and a contact lens.

10. The method according to claim 1, wherein said administering is systemic administration of said compound.

11. The method according to claim 10, wherein said systemic administration is administration of a liquid/liquid suspension of said compound via nose drops or nasal spray, or administration of a nebulized liquid to oral or nasopharyngeal airways of said subject, such that a therapeutically effective amount of said compound contacts retinal tissues of said subject via systemic absorption and circulation.

12. The method according to claim 10, wherein said systemic administration of said compound is accomplished by administering an oral form of said compound, such that a therapeutically effective amount of said compound contacts retinal tissues of said subject via systemic absorption and circulation.

13. The method according to claim 12, wherein said oral form is a chewable gum.

14. The method according to claim 10, wherein said systemic administration is administration of an injectable form of said compound, such that a therapeutically effective amount of said compound contacts retinal tissues of said subject via systemic absorption and circulation.

15. The method according to claim 10, wherein said systemic administration is administration of a suppository form of said compound, such that a therapeutically effective amount of said compound contacts retinal tissues of said subject via systemic absorption and circulation.

16. The method according to claim 10, wherein said systemic administration is administration of an intraoperative instillation of a gel, cream, powder, foam, crystals, liposomes, spray or liquid suspension form of said compound, such that a therapeutically effective amount of said compound contacts the retinal issues of said subject via systemic absorption and circulation.

17. The method according to claim 10, wherein said systemic administration is administration of said compound in a form of a transdermal patch or a transdermal pad, such that a therapeutically effective amount of said compound contacts the retina tissues of said subject via systemic absorption and circulation.

18. The method according to claim 1, wherein said retinal degenerative disease is dry macular degeneration, Stargardt's disease, glaucoma, retinitis pigmnentosa, or optic nerve degeneration.

19. The method according to claim 1, wherein said retinal degenerative disease is an inflammation-induced retinal degenerative disease caused by viral-, bacterial- or toxin.

20. The method according to claim 1, wherein said retinal degenerative disease is an inflammation-induced retinal degenerative disease, which results in optic neuritis.

21. The method according to claim 4, wherein said compound of Formula IVa is dCP$_4$U.

* * * * *